(12) United States Patent
Hein et al.

(10) Patent No.: US 8,116,426 B2
(45) Date of Patent: Feb. 14, 2012

(54) COMPUTED TOMOGRAPHY DEVICE AND METHOD USING CIRCULAR-PIXEL POSITION-ADAPTIVE INTERPOLATION

(75) Inventors: Ilmar Hein, Chicago, IL (US); Aleksandr Zamyatin, Buffalo Grove, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 454 days.

(21) Appl. No.: 12/268,889

(22) Filed: Nov. 11, 2008

(65) Prior Publication Data

US 2010/0119034 A1    May 13, 2010

(51) Int. Cl.
*A61B 6/03* (2006.01)
(52) U.S. Cl. .................. 378/19; 378/4; 382/131
(58) Field of Classification Search ............... 378/4, 19, 378/901; 382/131
See application file for complete search history.

(56) References Cited

U.S. PATENT DOCUMENTS

| | | | | |
|---|---|---|---|---|
| 6,137,856 | A * | 10/2000 | Lin | 378/4 |
| 2006/0104408 | A1* | 5/2006 | Thibault et al. | 378/4 |
| 2006/0104410 | A1* | 5/2006 | Sauer et al. | 378/4 |
| 2009/0202036 | A1* | 8/2009 | Ziegler et al. | 378/19 |

OTHER PUBLICATIONS

Ziegler et al., Efficient projection and backprojection scheme for spherically symmetric basis functions in divergent beam geometry, 2006, Medical Physics, vol. 33, No. 12, pp. 4653-4663.*

* cited by examiner

*Primary Examiner* — Edward Glick
*Assistant Examiner* — John Corbett
(74) *Attorney, Agent, or Firm* — Oblon, Spivak, McClelland, Maier & Neustadt, L.L.P.

(57) ABSTRACT

A method of computed-tomography and a computed-tomography apparatus where a interpolation kernel width is adaptively determined as a function of the distance from the x-ray source to the reconstruction pixel. The width of the kernel is the projection of the reconstruction pixel on the detector. The method can be implemented in the channel direction. The method can also be implemented in the segment direction, or in the channel and segment directions at the same time. Backprojection is performed using the adaptive kernel width and may by used with helical and circular scanning, and with cone-beam or fan beam x-ray CT.

4 Claims, 8 Drawing Sheets

FIG. 1

BACKGROUND ART

FIG. 2

BACKGROUND ART

FIG. 3

BACKGROUND ART

COMPUTED TOMOGRAPHY DEVICE AND METHOD USING CIRCULAR-PIXEL POSITION-ADAPTIVE INTERPOLATION

BACKGROUND OF THE INVENTION

1. Field of the Invention

The present invention relates to helical and circular x-ray computed tomographic (CT) imaging, and in particular to CT imaging with adaptive interpolation.

2. Discussion of the Background

Figure 1:
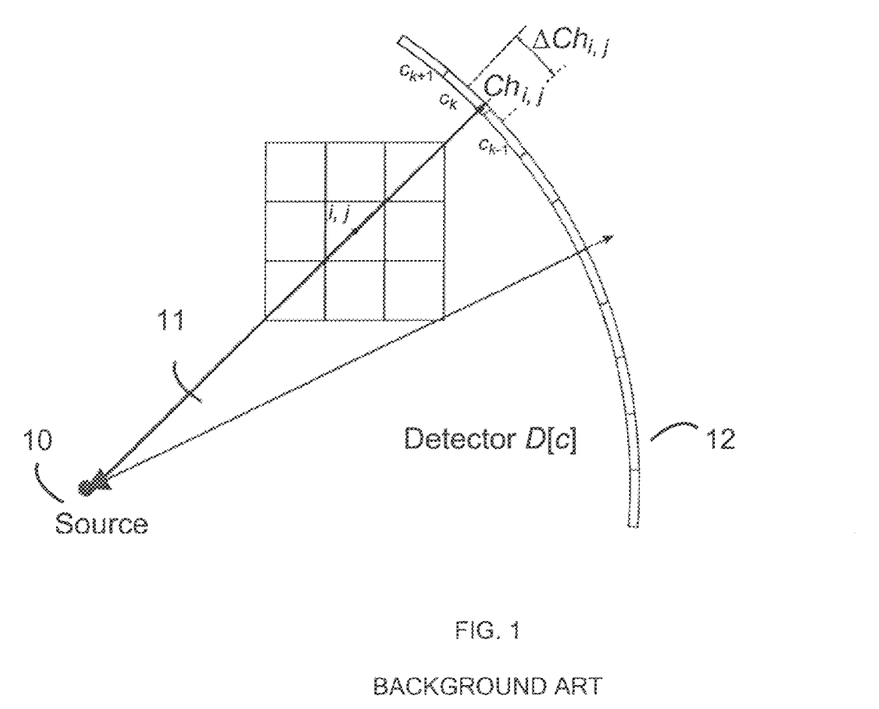
FIG. 1 is a diagram illustrating conventional pixel-driven backprojection.

There are several methods of backprojection. A common method is pixel-driven backprojection illustrated in FIG. 1. A ray 11 is drawn from the source 10 through the center of the reconstruction pixel at (i,j) to the detector array 12. Ray 11 intersects detector 12 at floating point channel index $Ch_{i,j}$ on channel $c_k$. The value assigned to the pixel is a linear interpolation of the values of the detector the ray intersects and the adjacent elements:

$$V(i,j) = w_{k-1} \cdot D(c_{k-1}) + w_k \cdot D(c_k) + w_{k+1} \cdot D(c_{k+1}) \quad (1)$$

where $c_k$ is the channel of intersection and $w_{k-1}+w_k+w_{k+1}=1$. For typical linear interpolation, the interpolation kernel width $\Delta Ch$ is fixed at one channel and only two detector elements are used (either $w_{k-1}$ or $w_{k+1}$ is zero). A nearest neighbor implementation has $w_{k+1}=w_{k-1}=0$ and $w_k=1$. Another pixel-driven method adjusts the weights such that interpolation kernel locations on the detector are always adjacent, as described in U.S. Pat. No. 6,724,856.

Pixel-driven methods are easy to implement. However, the disadvantage is that actual projection of the pixel onto the detector array is not used to compute V(i,j). For large pixel sizes, the projection of the pixel onto the array will be larger than one channel, meaning that too few detector elements contribute to V(i,j), and the signal-to-noise ratio (SNR) will be poorer. For small pixel sizes the projection of the pixel onto the array is smaller than one channel, causing a loss of lateral resolution.

Figure 2:
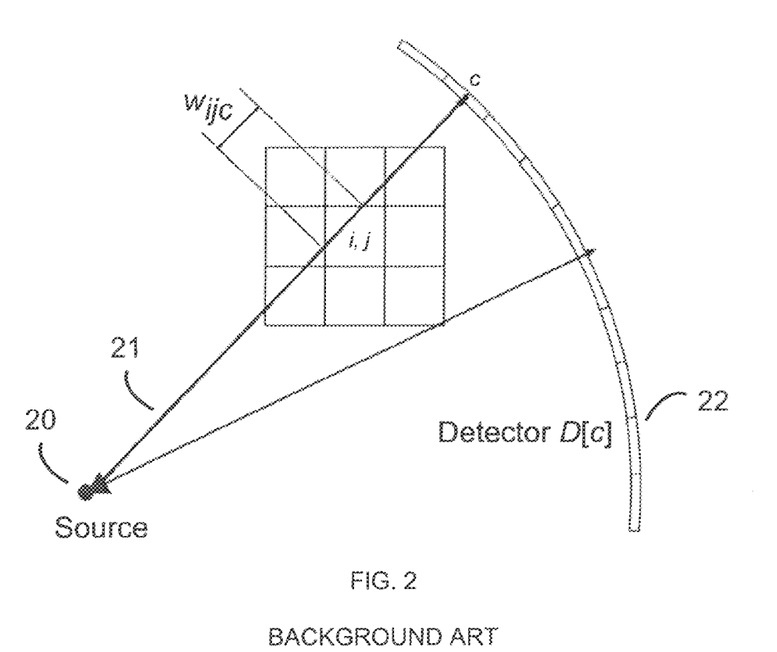
FIG. 2 is a diagram illustrating conventional ray-driven backprojection.

Another backprojection method is ray-driven backprojection. This technique is shown in FIG. 2 and described in Barrett, Harrison and Swindell, William, "*Radiological Imaging: The Theory of Image Formation, Detection, and Processing*," New York: Academic Press, 1981, pp. 421-422. In this case the backprojection ray 21 is drawn from the source 20 to the centers (indicated as c) of detector elements in the detector array 22, and the contribution weight $w_{ijc}$ of the detector element to pixels in the ray path is determined from the length of the ray within the pixel, as follows:

$$V(i,j) = V(i,j) + w_{ijc} \cdot D(c) \quad (2)$$

Other ray driven methods perform linear interpolation between two pixels for each row or column intersected by the projection line, as described in Joseph P, "*An improved algorithm for reprojecting rays through pixel images*," IEEE Trans. Med. Imaging 1, pp. 192-196 (1982).

Figure 3:
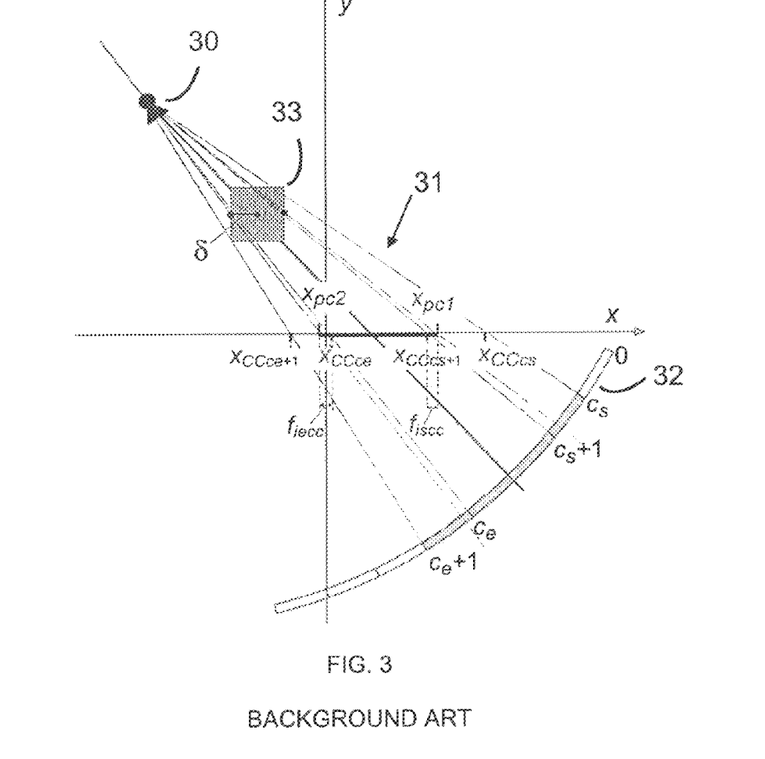
FIG. 3 is a diagram illustrating conventional distance-driven backprojection.

A third technique, distance-driven backprojection, maps the boundaries of the pixels and the detector elements onto a common axis (referred to as centering), and the amount of overlap is used as the backprojection weight, as shown in FIG. 3. Rays 31 from source 30 strike array 32. See U.S. Pat. No. 7,227,982 and De Man, Bruno, and Basu, Samit, "*Distance-driven projection and backprojection in three dimensions*," Phys Med Biol 49, pp. 2463-2475 (2004).

The pixel 33 is assumed to be square with a half-width δ, and the edges of the square pixel are in the x-ray beam 31 from source 30 are projected to points $x_{pc1}$ and $x_{pc2}$ on the common centering x axis. Similarly, the boundaries of detectors c are projected to positions xcc on the x axis. In FIG. 3, channel boundaries $c_s$ to $c_{e+1}$ are projected to positions $xcc_{cs}$ to $xcc_{ce+1}$ on the centering axis. The interpolation kernel width is the overlap of $x_{pc1}$ to $x_{pc2}$ with $xcc_{cs}$ to $xcc_{ce+1}$:

$$V(i,j) = \frac{f_{iscc} \cdot D[c_s]}{(ycc_{ks} - ycc_{ks+1})} + \frac{f_{iecc} \cdot D[c_e]}{(ycc_{ke} - ycc_{ke+1})} + \sum_{c'=c_s+1}^{c_e-1} D[c'] \quad (3)$$

The advantage of this method is that the projection of the pixel onto the detector is used to determine the interpolation kernel width, yielding improved SNR at large pixel sizes and improved resolution at smaller pixel sizes. The disadvantage to this method is that both the channels and pixels must be projected onto a centering axis (typically the y or x axis), which makes processing more complex. Furthermore, the resulting interpolation kernel width is a function of view.

SUMMARY OF THE INVENTION

The present invention, in one embodiment, is directed to a computed-tomography method including determining a channel position located on an x-ray detector using a linear path from an x-ray source through a backprojection pixel, and determining an interpolation kernel width using a distance from the source to the backprojection pixel.

In another embodiment, the present invention is directed to an apparatus having an x-ray source, an x-ray detector having channels and segments, a signal processing unit connected to receive data collected the detector, and configured to determine a channel position on the detector located on a linear path from the x-ray source through a backprojection pixel and determine an interpolation kernel width using a distance from the source to the backprojection pixel.

The present invention may also be directed to a computer-readable medium containing instructions, wherein the instructions, when executed by a computer, perform a method including determining a channel position located on a linear path from an x-ray source through a backprojection pixel, and determining an interpolation kernel width using a distance from the source to the backprojection pixel.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 4:
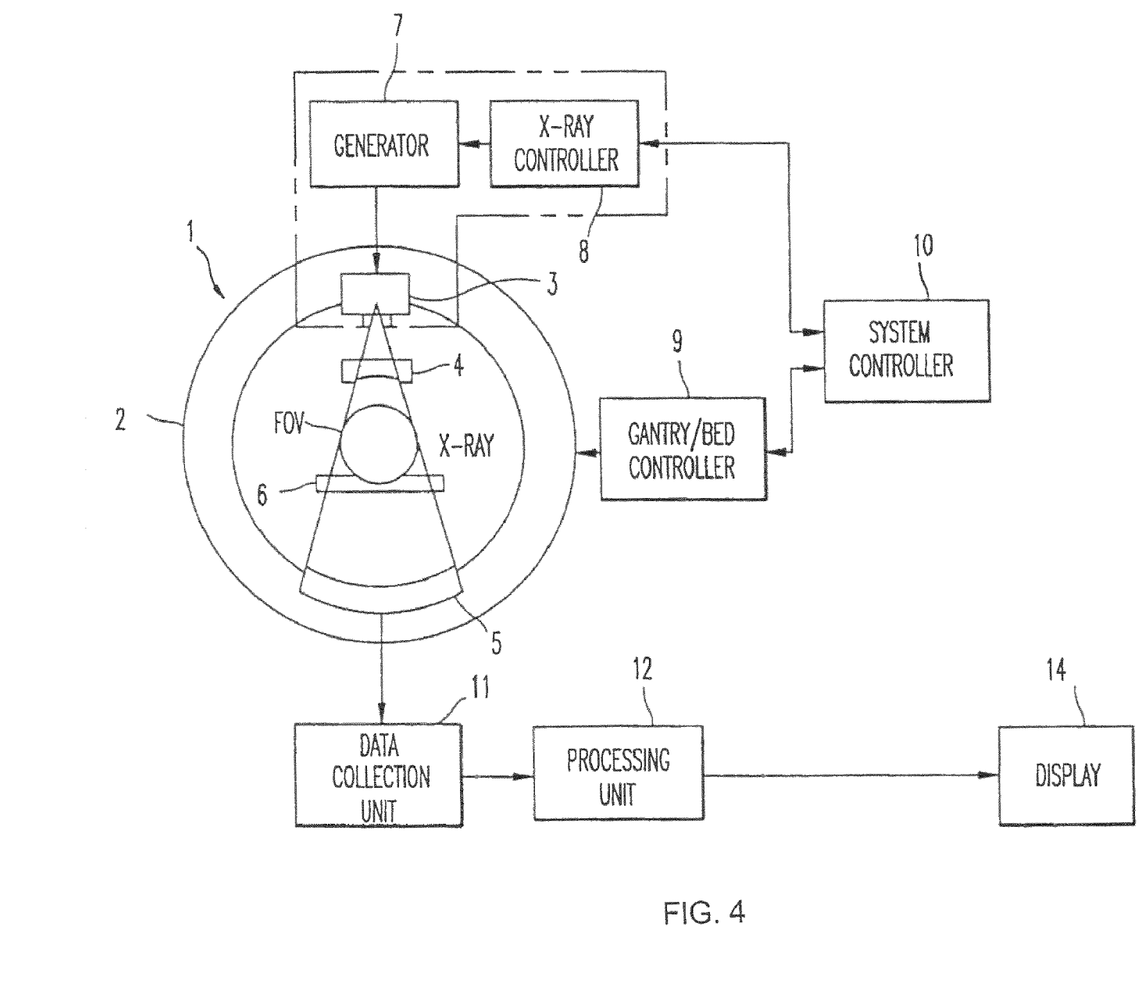
FIG. 4 is a diagram of a system according to the invention.

FIG. 4 shows an x-ray computed tomographic imaging device according to the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3. The source may also be scanned circularly.

The output signal of two-dimensional array type x-ray detector 5 is amplified by a data collection unit 11 for each channel and converted to a digital signal, to produce projection data. The projection data output from data collection unit 11 is fed to processing unit 12. Processing unit 12 performs various processing using the projection data. Unit 12 performs interpolation, backprojection and reconstruction, as described in more detail below. Unit 12 determines backprojection data reflecting the x-ray absorption in each voxel. In the helical scanning system using a cone-beam of x-rays, the imaging region (effective field of view) is of cylindrical shape of radius o) centered on the axis of revolution. Unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 5:
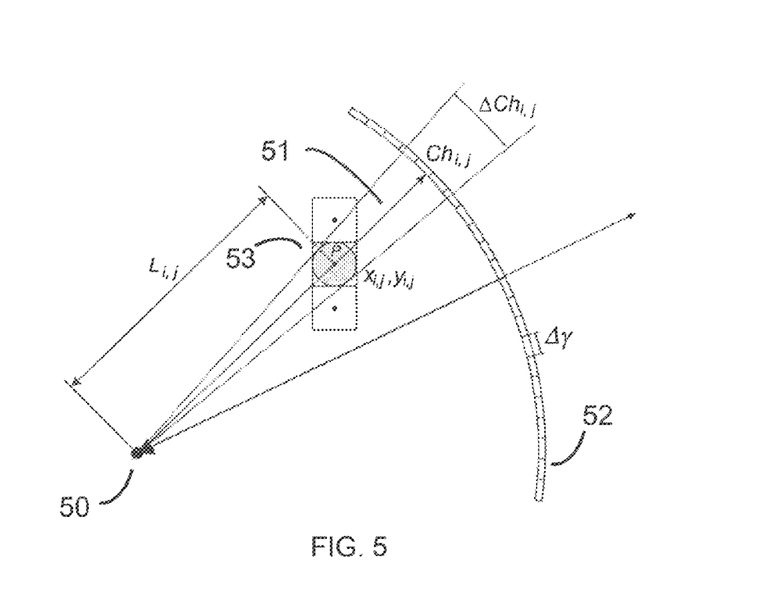
FIG. 5 is a diagram illustrating possible axial spatial orientations for adjacent views with resulting interpolated views.

The basic geometry of the backprojection according to the invention is illustrated in FIG. 5. The backprojection according to the invention may by used with helical and circular scanning, and with cone-beam or fan beam x-ray CT. It incorporates the pixel-driven attribute of tracing a line 51 from the source 50 through the center of the pixel 53 (having radius P) to the detector 52 to determine the backprojection position $Ch_{i,j}$, and adaptively determines the interpolation kernel width $\Delta Ch$ as a function of the source to pixel distance L assuming the pixel has a circular shape. The backprojection according to the invention does not require projection of pixels and detector boundaries onto a centering axis, yet retains the advantage of distance-based backprojection; i.e., improved signal-to-noise ratio (SNR) at large pixel sizes and improved resolution at smaller pixel sizes.

Figure 6:
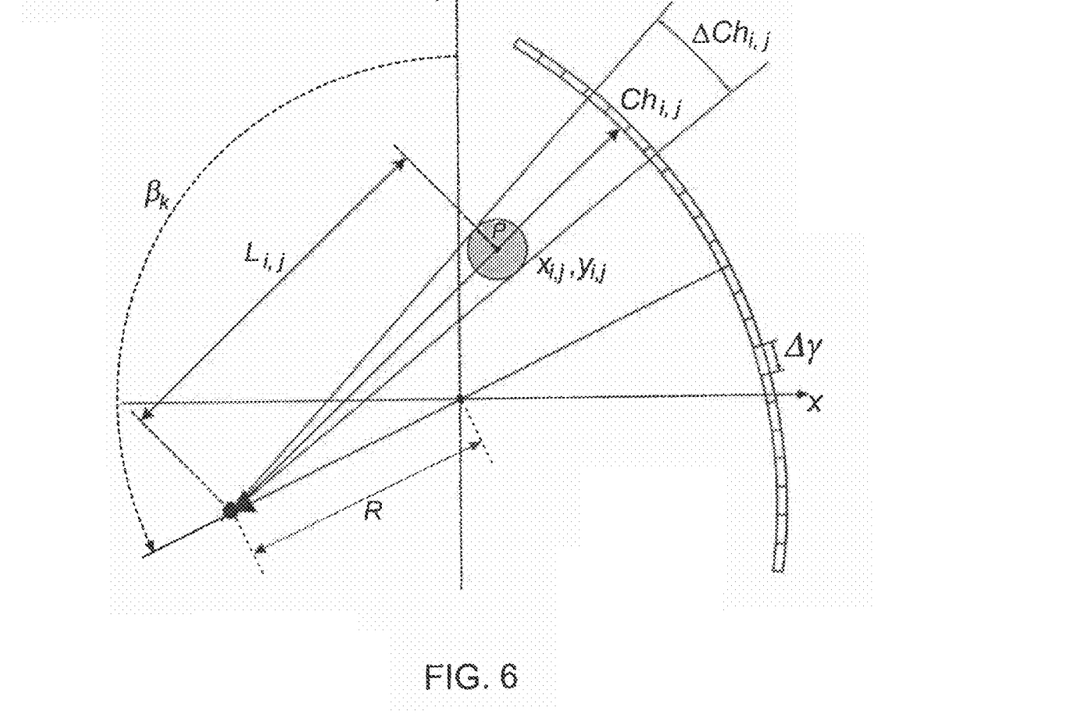
FIG. 6 is a diagram illustrating backprojection according to the invention.

For a 2-D implementation, the adaptive kernel is applied only in the channel direction, and bilinear interpolation in the segment direction. The backprojection according to the invention in the channel direction is shown in more detail in FIG. 6, with segments omitted for clarity. The pixel is assumed to have a circular shape with center at position $x_{i,j}$, $y_{i,j}$ and radius P:

$$P = \frac{FOV}{2 \cdot MATRIX} \quad (4)$$

where FOV is the reconstruction field of view and MATRIX is the reconstructed image matrix size. The floating point channel position $Ch_{i,j}$ (in units of channels) is determined in the same manner as for a pixel-driven method:

$$Ch_{i,j,k} = \frac{1}{\Delta\gamma}\tan^{-1}\left[\frac{x_{i,j}\cos\beta_k + y_{i,j}\sin\beta_k}{R + x_{i,j}\sin\beta_k - y_{i,j}\cos\beta_k}\right] \quad (5)$$

where $\Delta\gamma$ the angular channel width, $\beta_k$ is the view angle at view k, and R is the source to isocenter distance, where the isocenter is the gantry rotation axis. The projection of the circular pixel determines the adaptive channel interpolation kernel width (in units of channels), which is given by:

$$\Delta Ch_{i,j,k} = \frac{2P}{\Delta\gamma \cdot L_{i,j,k}} \quad (6)$$

where $$L_{i,j,k}(x_{i,j}, y_{i,j}, \beta_k) = \sqrt{(R\sin\beta_k + x_{i,j})^2 + (R\cos\beta_k - y_{i,j})^2} \quad (7)$$

Figure 7:
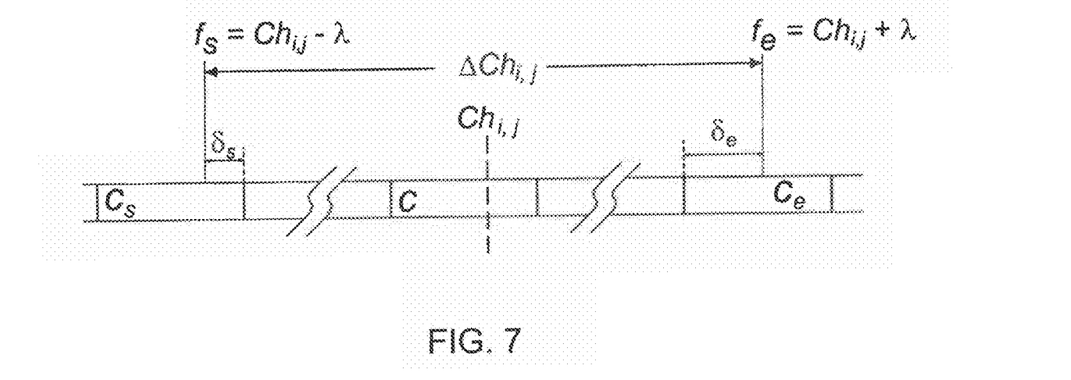
FIG. 7 is a diagram illustrating calculation of the backprojection value.

Calculation of the channel interpolated backprojection value is illustrated in FIG. 7 Here, c is an integer and represents the channel number that a backprojection ray intersects. In this example, it is assumed that the indexing of the channels is such that the first channel is located at c=0, and that a ray intersecting channel 0 exactly in the center will have floating point position 0.5 (i.e., possible range of positions for channel 0 is 0.0 to 0.9999 . . . ) Other indexing schemes may have the center of channel 0 at 0.0, with a possible range of positions from −0.5 to +0.49999 . . . . If a different indexing scheme is used, Eq. 5 will be accordingly altered by adding a shift amount.

$$PDI_{Ch_{i,j,k}} = \begin{cases} PD(c) & \text{if } c_s = c \text{ and } c_e = c \\ \frac{1}{\Delta Ch_{i,j,k}}\left(\delta_s \cdot PD(c_s) + \delta_e \cdot PD(c_e) + \sum_{c'=c_s+1}^{c_e-1} PD(c')\right) & \text{otherwise} \end{cases} \quad (8)$$

where PD( ) is raw projection data, PDI is interpolated value of projection data, $c_s$, c, and $c_e$ are integer starting, center, and ending channel indexes and $$\lambda = \frac{\Delta Ch_{i,j,k}}{2} \quad (9)$$

$$f_s = Ch_{i,j} - \lambda \quad (10)$$

$$f_e = Ch_{i,j} + \lambda \quad (11)$$

$$c_s = \text{int}(f_s) \quad (12)$$

$$c_e = \text{int}(f_e) \quad (13)$$

$$\delta_s = c_{s+1} - f_s \quad (14)$$

$$\delta_e = f_e - c_e \quad (15)$$

Figure 8:
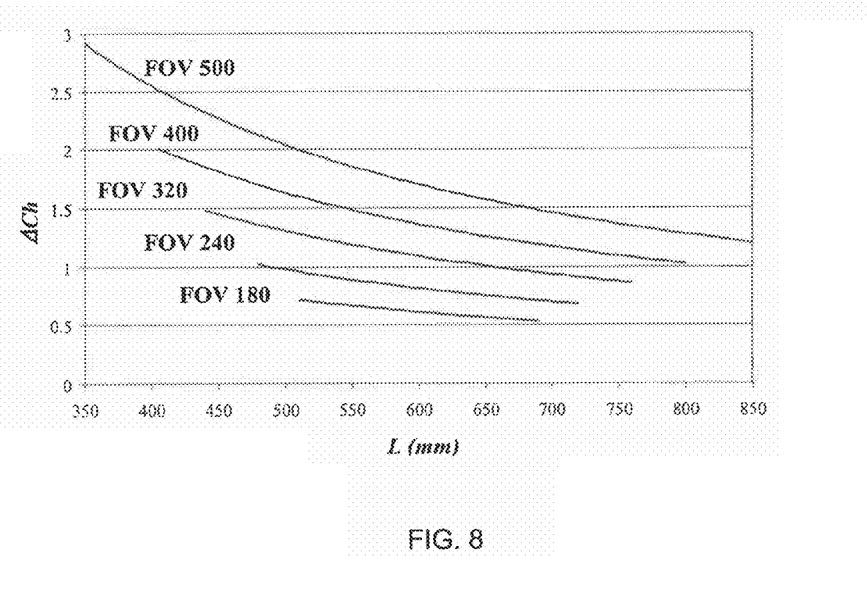
FIG. 8 is a graph illustrating backprojection according to the invention for different field of views.

FIG. 8 shows an example of the interpolation kernel $\Delta Ch$ as a function of L for various FOV sizes. For standard pixel-driven backprojection, $\Delta Ch$ is equal to 1.0. Smaller FOVs are typically used to visualize smaller structures, where a higher resolution is desirable. For small FOVs of 240 and less, $\Delta Ch < 1$, which provides a better resolution. For larger FOVs, resolution is usually not the issue. Here $\Delta Ch > 1$, which provides a better signal-to-noise ratio, since more channels are used in the interpolation as well as better aliasing artifact.

Figure 9:
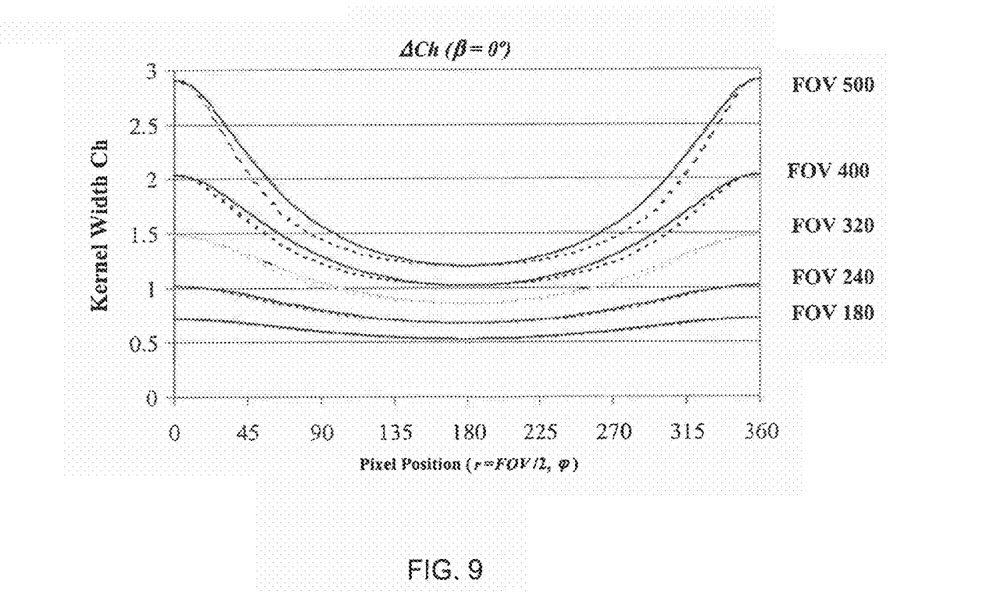
FIG. 9 is a graph illustrating a comparison between backprojection according to the invention and distance-driven backprojection at different field of views.
Figure 10A:
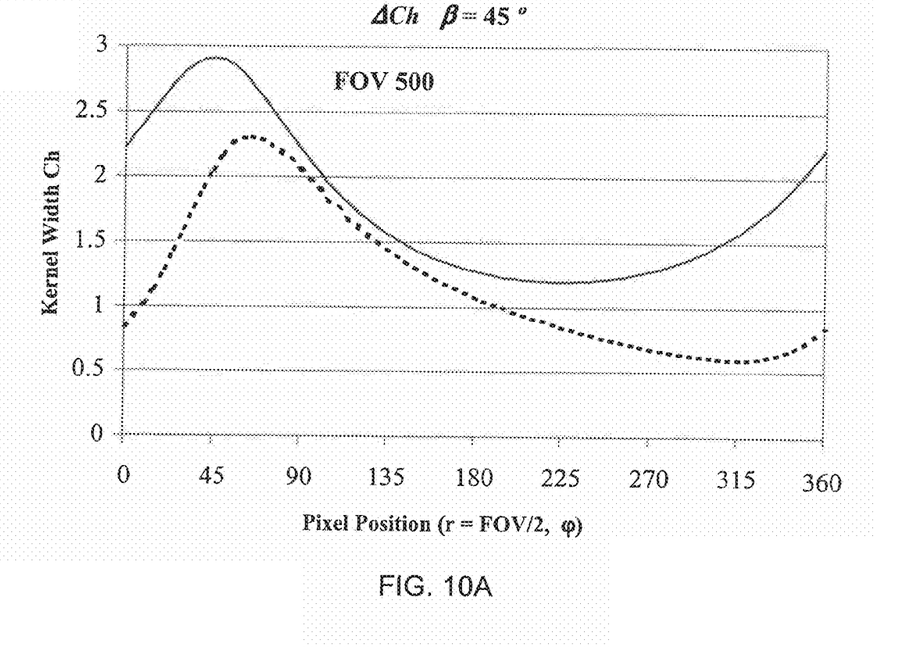
FIGS. 10A-10E are graphs illustrating a comparison between backprojection according to the invention and distance-driven backprojection at different field of views.
Figure 10B:
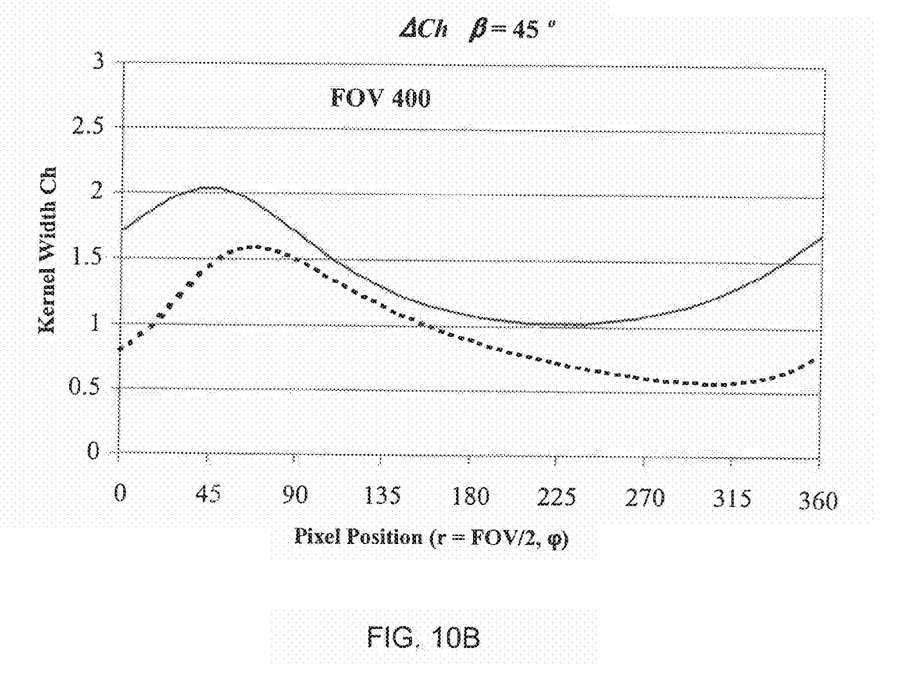
Figure 10C:
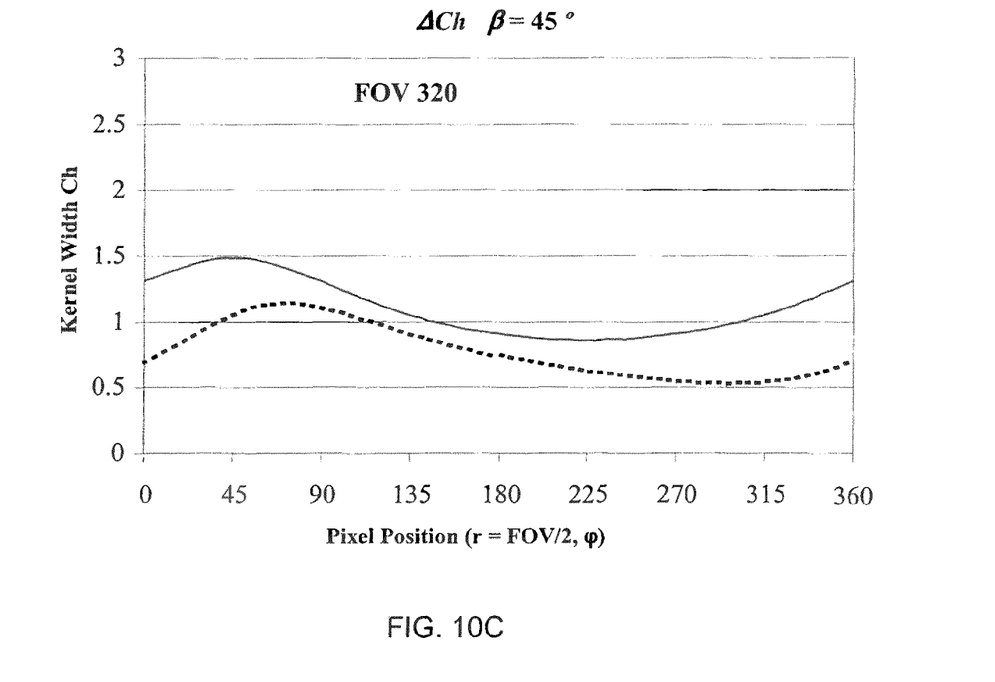
Figure 10D:
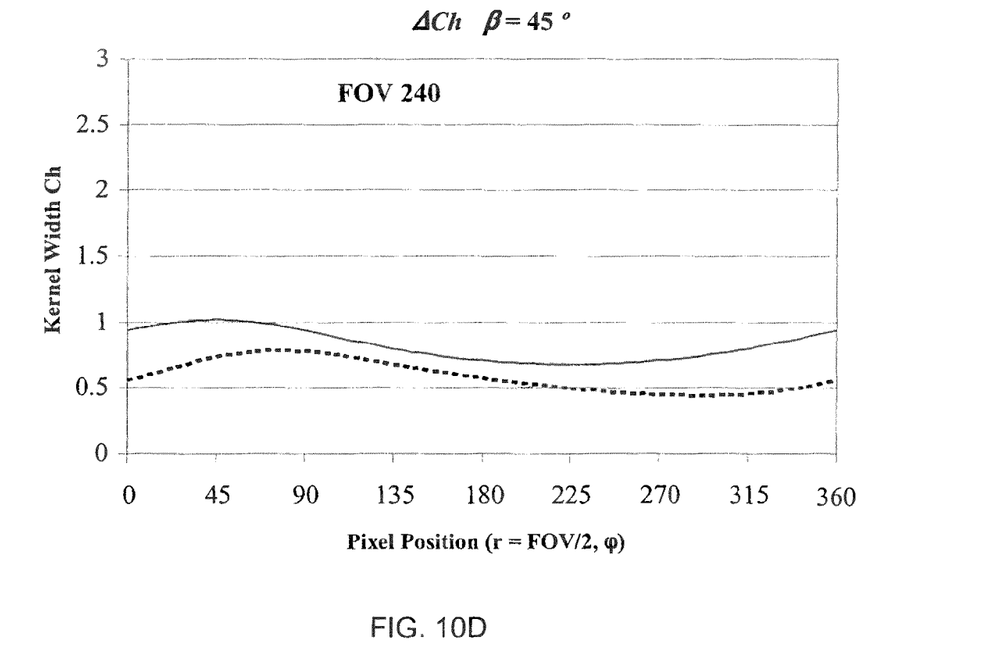
Figure 10E:
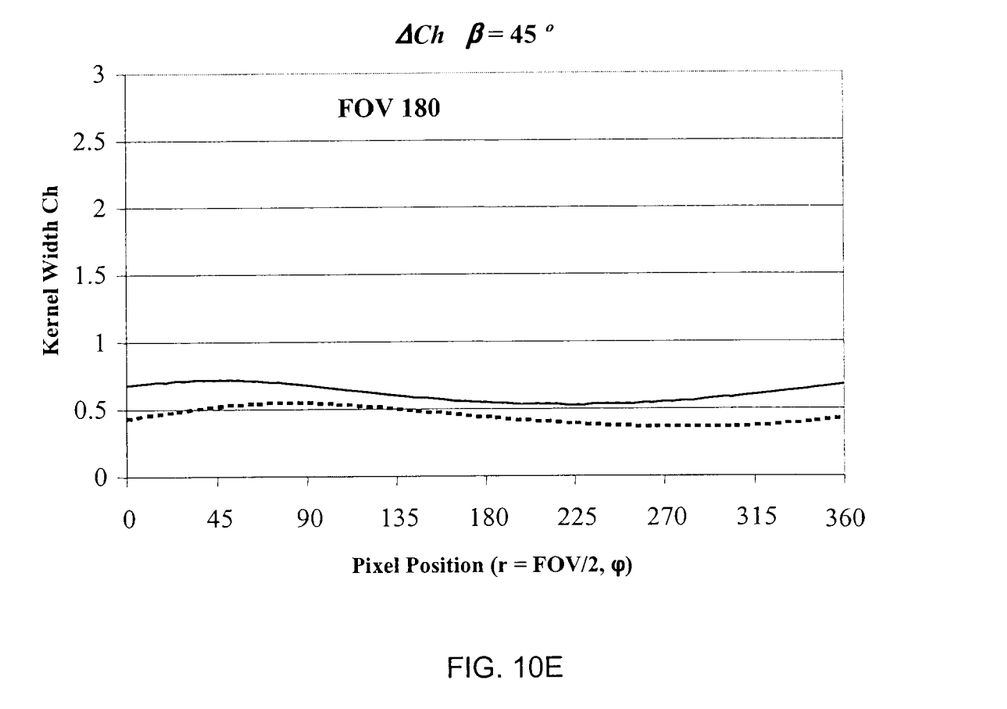
Figure 11:
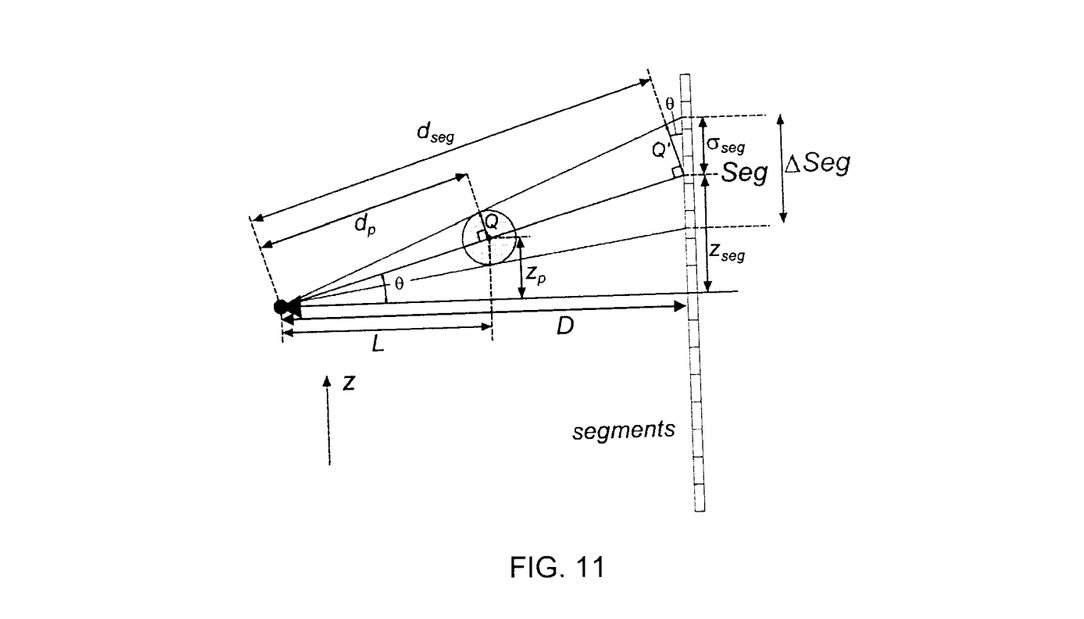
FIG. 11 is a diagram illustrating a second embodiment of the invention.

FIG. 9 shows a comparison of $\Delta Ch$ between the present invention (solid lines) and distance driven backprojection (DDBPJ, dashed lines) at extremes of view angle $\beta = 0°$ and $\beta = 45°$ (which are extremes for DDBPJ for the centering process). These are shown as a function of angular pixel position $\phi$ at radii of various FOVs. Overall, $\Delta Ch$ for the present invention is somewhat larger than DDBPJ for a given FOV and pixel position, but will have similar image quality.

FIGS. 8 and 9 show that the method according to the invention can provide similar performance in terms of images compared to the conventional methods, while the method according to the invention.

In the first embodiment, the method is implemented in the channel direction. In an alternate embodiment, the method can be implemented in the segment direction by assuming the voxel is circular in z and calculating the projection of the circle across the segments in the z direction, as shown in FIG. 10. Q is the pixel radius in z and is equal to the reconstruction slice spacing (though in other embodiments it can be calculated differently). FIGS. 10A-E show results for FOVs of 500, 400, 320, 240 and 180, respectively. The solid lines represent the present invention and the dashed lines show, for comparison, distance driven backprojection.

The floating point segment position is determined exactly the same as it is for the pixel-driven method:

$$z_{seg} = \frac{D \cdot z_p}{L} \quad (16)$$

where $z_{seg}$ is the distance from the then center of the detector to the backprojection segment location, D is the source to detector distance and is $z_p$ is the z distance of the reconstruction pixel from the source-detector plane at view k. For circular scanning this is independent of view and for helical it is a function of view. The floating point segment position Seg is given by $$Seg = \frac{z_{seg}}{w} \quad (17)$$

where w is the segment width at isocenter.

The adaptive segment interpolation kernel width $\Delta Seg$ (in units of segments) given by:

$$\Delta Seg = \frac{2\sigma_{seg}}{w} \quad (18)$$

where $$\sigma_{seg} = Q \cdot \cos\theta \frac{d_{seg}}{d_p} \quad (19)$$

$$d_{seg} = \sqrt{D^2 + z_{seg}^2} \quad (20)$$

$$d_p = \sqrt{L^2 + z_p^2} \quad (21)$$

$$\theta = \tan^{-1}\frac{z_p}{L} \quad (22)$$

Calculation of the segment backprojection value is calculated in the same manner as for the channels as in FIG. 7 and Eq. 8, substituting segments for channels.

In a third embodiment, the method can be implemented for both the channel and segment directions at the same time. This is the 3-D case, where the circular pixel is now a spherical voxel with radius S. Equations (6-15) are used to calculate channel direction projection with P=S and equations (16-22) for segment direction, with Q=S. This embodiment can be used for full cone-beam detectors.

The invention may also be embodied in the form a computer-readable medium containing a stored program to cause a computer to carry out the various operations and functions described above.

Numerous other modifications and variations of the present invention are possible in light of the above teachings. This document and equations have been developed for a curved detector array. For example, a flat or other detector array shape can be implemented. It is therefore to be understood that within the scope of the appended claims, the invention may be practiced otherwise than as specifically described herein.

The invention claimed is:

1. A computed-tomography method, comprising:
   determining a channel position located on an x-ray detector using a linear path from an x-ray source through a backprojection pixel;
   determining an interpolation kernel width using a distance from said source to said backprojection pixel;
   determining a radius P of said pixel having a circular shape with a center at position $x_{i,j}$, $y_{i,j}$ as $$P = \frac{FOV}{2 \cdot \text{MATRIX}}$$

where FOV is a reconstruction field of view and MATRIX is a reconstructed image matrix size;
   determining a floating point channel position $Ch_{i,j}$ as:

$$Ch_{i,j,k} = \frac{1}{\Delta\gamma}\tan^{-1}\left[\frac{x_{i,j}\cos\beta_k + y_{i,j}\sin\beta_k}{R + x_{i,j}\sin\beta_k - y_{i,j}\cos\beta_k}\right]$$

where $\Delta\gamma$ is an angular channel width, $\beta_k$ is a view angle at view k, and R is a distance from said x-ray source to isocenter distance; and determining said kernel width $\Delta Ch_{i,j}$ as:

$$\Delta Ch_{i,j,k} = \frac{2P}{\Delta\gamma \cdot L_{i,j,k}}$$

where $$L_{i,j,k}(x_{i,j}, y_{i,j}, \beta_k) = \sqrt{(R\sin\beta_k + x_{i,j})^2 + (R\cos\beta_k - y_{i,j})^2}.$$

2. A method as recited in claim 1, comprising:
   calculating a backprojection value PDI as:

$$PDI_{CH_{i,j,k}} = \begin{cases} PD(c) & \text{if } c_s = c \text{ and } c_e = c \\ \frac{1}{\Delta Ch_{i,j,k}}\left(\delta_s \cdot PD(c_s) + \delta_e \cdot PD(c_e) + \sum_{c'=c_s+1}^{c_e-1} PD(c')\right) & \text{otherwise} \end{cases}$$

where PD( ) is raw projection data, $c_s$, c, and $c_e$ are integer starting, center, and ending channel indexes of a detector, and $$\lambda = \frac{\Delta Ch_{i,j,k}}{2}$$

$$f_s = Ch_{i,j} - \lambda$$

-continued $$f_e = Ch_{i,j} + \lambda$$

$$c_s = \text{int}(f_s)$$

$$c_e = \text{int}(f_e)$$

$$\delta_s = c_{s+1} - f_s,$$

and $$\delta_e = f_e - c_e.$$

3. A non-transitory computer-readable medium containing instructions, wherein the instructions, when executed by a computer, perform a method comprising:
   determining a channel position located on a linear path from an x-ray source through a backprojection pixel;
   determining an interpolation kernel width using a distance from said source to said backprojection pixel;
   determining a radius P of said pixel having a circular shape with a center at position $x_{i,j}$, $y_{i,j}$ as $$P = \frac{FOV}{2 \cdot \text{MATRIX}}$$

where FOV is a reconstruction field of view and MATRIX is a reconstructed image matrix size;

determining a floating point channel position $Ch_{i,j}$ as:

$$Ch_{i,j,k} = \frac{1}{\Delta\gamma}\tan^{-1}\left[\frac{x_{i,j}\cos\beta_k + y_{i,j}\sin\beta_k}{R + x_{i,j}\sin\beta_k - y_{i,j}\cos\beta_k}\right]$$

where $\Delta\gamma$ is an angular channel width, $\beta_k$ is a view angle at view k, and R is a distance from said x-ray source to isocenter distance; and determining said kernel width $\Delta Ch_{i,j}$ as:

$$\Delta Ch_{i,j,k} = \frac{2P}{\Delta\gamma \cdot L_{i,j,k}}$$

where $$L_{i,j,k}(x_{i,j}, y_{i,j}, \beta_k) = \sqrt{(R\sin\beta_k + x_{i,j})^2 + (R\cos\beta_k - y_{i,j})^2}.$$

4. A non-transitory medium as recited in claim 3, wherein said method further comprises:
   calculating a backprojection value PDI as:

$$PDI_{CH_{i,j,k}} = \begin{cases} PD(c) & \text{if } c_s = c \text{ and } c_e = c \\ \frac{1}{\Delta Ch_{i,j,k}}\left(\delta_s \cdot PD(c_s) + \delta_e \cdot PD(c_e) + \sum_{c'=c_s+1}^{c_e-1} PD(c')\right) & \text{otherwise} \end{cases}$$

where PD( ) is raw projection data, $c_s$, c, and $c_e$ are integer starting, center, and ending channel indexes of a detector, and $$\lambda = \frac{\Delta Ch_{i,j,k}}{2}$$

$$f_s = Ch_{i,j} - \lambda$$

$$f_e = Ch_{i,j} + \lambda$$

$$c_s = \text{int}(f_s)$$

$$c_e = \text{int}(f_e)$$

$$\delta_s = c_{s+1} - f_s,$$

and $$\delta_e = f_e - c_e.$$

* * * * *